(12) United States Patent
Beckett et al.

(10) Patent No.: US 6,451,732 B1
(45) Date of Patent: Sep. 17, 2002

(54) HERBICIDAL COMPOSITIONS OF GLYPHOSATE TRIMESIUM

(75) Inventors: Thomas Homer Beckett, Champaign, IL (US); Stott Willie Howard, Antioch, CA (US)

(73) Assignee: Syngenta, Limited (GB)

( * ) Notice: Subject to any disclaimer, the term of this patent is extended or adjusted under 35 U.S.C. 154(b) by 0 days.

(21) Appl. No.: 09/580,674

(22) Filed: May 30, 2000

Related U.S. Application Data

(60) Provisional application No. 60/137,666, filed on Jun. 4, 1999.

(51) Int. Cl.$^7$ ................................................ A01N 57/00
(52) U.S. Cl. ....................................................... 504/128
(58) Field of Search ......................................... 504/128

(56) References Cited

U.S. PATENT DOCUMENTS 5,985,799 A * 11/1999 Tseng .......................... 504/281
6,117,820 A * 9/2000 Cutler et al. ................. 504/206

FOREIGN PATENT DOCUMENTS

| EP | 182120 | * | 5/1986 |
| WO | 9731535 | * | 9/1997 |
| WO | 9909830 | * | 3/1999 |

OTHER PUBLICATIONS

EPA, Sulfosate; pesticide tolerance, Fed. Regist., 1999, vol. 64 (112), 31505–11.*

* cited by examiner

*Primary Examiner*—Alton Pryor
(74) *Attorney, Agent, or Firm*—William A. Teoli, Jr.; Rose M. Allen

(57) ABSTRACT

Herbicidal compositions containing glyphosate trimesium and an antidotally effective amount of a photosystem II inhibitor compound to reduce the infrequent expression of short term transitory cosmetic plant effect to glyphosate tolerant soybeans from glyphosate trimesium. Methods for reducing the infrequent expression of short term transitory cosmetic plant effect to glyphosate tolerant crop plants due to glyphosate trimesium are also described.

16 Claims, No Drawings

HERBICIDAL COMPOSITIONS OF GLYPHOSATE TRIMESIUM

The application claims the benefit of Ser. No. 60/137,666 Jun. 4, 1999.

FIELD OF THE INVENTION

This invention relates to herbicide compositions and methods of use and, more particularly, to certain herbicidal compositions comprising the trimethylsulphonium salt of N-phosphonomethylglycine (glyphosate trimesium) and an antidotally effective amount of an herbicide which functions as a photosystem II inhibitor.

BACKGROUND OF THE INVENTION

Glyphosate trimesium is well known as a highly active and effective herbicide which achieves excellent control of weed species together with an effective reduction in regrowth.

It is known that glyphosate trimesium and other glyphosate herbicides (i.e. salts of N-phosphonomethylglycine and phosphonomethylglycine acid) may injure crop plants at herbicide application rates needed to control weed growth. Until recently, glyphosate herbicides were unsuitable for controlling weeds in the presence of crops.

In order to take advantage of the excellent herbicidal effectiveness of glyphosate herbicides in the presence of growing crops, a number of crops, including corn, cotton, canola, sugar beet and soybean, have been genetically modified to be resistant to or tolerant of glyphosate herbicides. Genetic constructs and methods for producing glyphosate resistant plants are described inter alia in U.S. Pat. Nos. 4,940,835 and 5,633,435 and PCT application WO 98/44140.

Glyphosate tolerant crops are believed to be tolerant to the herbicidal effects of the N-phosphonomethylglycine anion of glyphosate herbicides, which anion is almost exclusively responsible for the herbicidal effects of glyphosate herbicides. However, the trimesium cation of glyphosate trimesium occasionally may exhibit short term transitory cosmetic effects on plants, including crop plants. Applications of the herbicide glyphosate trimesium over-the-top of a glyphosate tolerant crop may result in short term transitory cosmetic effects on the glyphosate tolerant crop. Although such effects are infrequent, transitory and do not have an impact on crop yield, it may be highly desirable for commercial purposes to reduce the short term transitory cosmetic effects on glyphosate tolerant crops caused by the trimesium cation of the herbicide glyphosate trimesium.

The present inventors have unexpectedly discovered that application of glyphosate trimesium in combination with an antidotally effective amount of a herbicide which is a photosystem II inhibitor safens glyphosate tolerant crops against the short term transitory cosmetic effects of the trimesium cation.

It has now been discovered that certain herbicide compounds when used in an antidotally effective amount are effective antidotes for the expression of short term transitory cosmetic effects on glyphosate tolerant soybean crops, which may be caused by the use of an herbicidally effective amount of glyphosate trimesium. It is, therefore, an object of the present invention to provide compositions of glyphosate trimesium in combination with another herbicide which is antidotally effective therefor, which compositions are useful to reduce the expression of short term transitory cosmetic effects on glyphosate tolerant soybeans, which may be due to glyphosate trimesium.

SUMMARY OF THE INVENTION

The present invention relates to herbicidal compositions containing glyphosate trimesium and an antidotal compound therefor to reduce the expression of short term transitory cosmetic effects on glyphosate tolerant soybean crops of glyphosate trimesium when used alone or in combination with other compounds as co-herbicides.

More particularly, the invention relates to a composition comprising:

(a) glyphosate trimesium; and
(b) an antidotally effective amount of an herbicide which is a photosystem 1I inhibitor which is antidotally effective for glyphosate trimesium applied to glyphosate tolerant soybeans.

The invention further relates to methods for the expression of short term transitory cosmetic effects on any glyphosate tolerant crop soybean crops, due to glyphosate trimesium, by applying an antidotally effective amount of a photosystem II inhibitor compound to the soil, crop or crop seed.

DETAILED DESCRIPTION OF THE INVENTION

The present invention provides a method of reducing the expression of short term transitory cosmetic effects at a genetically modified glyphosate tolerant soybean plant locus caused by glyphosate trimesium, which method comprises applying to the soybean plant locus at least one photosystem II inhibitor herbicide.

The present applicants have found, surprisingly, that the presence of at least one herbicide which functions as a photosystem II inhibitor allows any glyphosate tolerant soybean phytotoxicity caused by lyphosate trimesium to be reduced, while maintaining a good level of weed control. The method of the invention reduces the expression of short term transitory cosmetic plant effects by a safening effect of the photosystem II inhibitor.

As examples of herbicides which function as photosystem II inhibitors there may be mentioned diuron [3-(3,4-dichlorophenyl)-1,1-dimethylurea)], chlortoluron, isoproturon, linuron, tebuthiuron, bentazon, oxadiazon, bromacil, ametryne, atrazine, cyanazine, hexazinone, metribuzin, simazine, and terbuthylazine, all of which are commercially available herbicides. Bentazon is an especially preferred photosystem II inhibitor for use in the present invention.

Photosystem II inhibitors other than bentazon may be useful in the present invention to safen glyphosate tolerant soybeans against the short term transitory cosmetic effects which may be caused by glyphosate trimesium. However, some of the photosysteml inhibitors, such as metribuzon, may have a phytotoxic effect on soybean crops, particularly when applied postemergence. To be useful in the present invention, the photosystem II inhibitor must be used in a manner and in an amount such that the photosystem II inhibitor does not itself have a significant phytotoxic effect upon the glyphosate tolerant soybean crops.

The amount of photosystem II inhibitor used in the method of the present invention varies according to a number of parameters including the amount and rate of glyphosate trimesium applied and the climatic conditions prevailing. The selection of the specific photosytem II inhibitor for use in the method of the present invention, the manner in which it is to be applied and the determination of the amount which is antidotally effective can be readily performed in accordance with common practice in the art. As used therein, the term "antidotally effective amount" is an amount of a photosystem II inhibitor which is effective in reducing the expression of short term transitory cosmetic plant effects caused by glyphosate trimesium or the trimesium cation to a genetically modified, glyphosate tolerant soybean crop, and which does not itself have a significant phytotoxic effect on the glyphosate tolerant soybean crop.

In the method of the present invention, glyphosate trimesium is used in an "herbicidally effective amount." The term "herbicidally effective amount" describes an amount of glyphosate trimesium which is capable of adversely controlling or modifying plant growth. The actual amount used depends upon a number of factors including, for example, the identity of the plants whose growth is to be controlled or inhibited, weed susceptibility, method of application and overall cost considerations.

The application rate of the glyphosate trimesium herbicide is generally from about 280 to about 7840 grams active ingredient/hectare (g ai/ha), preferably from about 560 to about 5600 g ai/ha, more preferably from about 560 to about 3360 g ai/ha and most preferably from about 840 to about 2240 g ai/ha.

The application rate of the photosystem II inhibitor is generally from about 5 to about 300 g al/ha, preferably from about 10 to about 170 g ai/ha, more preferably from about 15 to about 100 g ai/ha and most preferably from about 15 to about 75 g ai/ha.

The ratio of glyphosate trimesium to the photosystem II inhibitor used in the method of this invention is preferably from about 10 to about 95 parts by weight of glyphosate trimesium per 1 part photosystem II inhibitor. When bentazon is the photosystem II inhibitor, typical field use rates will be about 32 to 64 g of bentazon/ha with about 750 to 1500 g glyphosate trimesium/ha, which corresponds to a weight ratio of about 47 to 12 parts glyphosate trimesium to 1 part bentazon.

Herbicidal compositions according to this invention may also contain one or more additional pesticidally active ingredients. Herbicides which may be used as co-herbicides with glyphosate trimesium with benefit in combination with a photosytem II inhibitor as described herein include, but are not limited to, chlorimuron-ethyl, fomesafen, fluazifop-p-butyl, mixtures of fluazifop-p-butyl and fenoxaprop-p-ethyl, thifensulfuron-methyl, imazethapyr, mixtures of chlorimuron-ethyl and thifensulfiron-methyl, and imazaquin.

Such combinations can be used to obtain selective weed control with minimal crop injury in several varieties of soybeans which have been genetically modified to be glyphosate tolerant. Insecticides, such as synthetic pyrethroids, and fungicides, such as carbamates and triazoles, may also be included in the herbicidal compositions of this invention.

Effective weed control coupled with low expression of short term transitory cosmetic plant effect is a result of treatment of a plant locus with a combination of glyphosate trimesium and an antidotally effective photosystem II inhibitor compound in accordance with the present invention. By application to the "plant locus" is meant application to the plant growing medium, such as soil, as well as to the seeds, emerging seedlings, roots, stems, leaves, or other plant parts. Such application can be preemergence or postemergence of the glyphosate tolerant soybeans.

The phrase "combination of glyphosate trimesium and an antidotally effective photosystem II inhibitor" includes various methods of treatment. For example, the soybean plant locus may be treated with a "tank-mix" composition containing a mixture glyphosate trimesium and the antidotally effective photosystem R inhibitor which is "in combination." Or, the soybean plant locus may be treated with the glyphosate trimesium and the photosystem II inhibitor separately so that the "combination" is made on the soybean plant parts or in the soil.

Also contemplated as a "combination" is a commercially-convenient association or presentation of herbicide and antidote. For example, the herbicide and antidote components in concentrated form may be contained in separate containers, but such containers may be presented for sale or sold together as a "combination." Or, the herbicide and antidote components in concentrated form may be in a mixture in a single container as a "combination." Either such a "combination" may be diluted or mixed with adjuvants suitable for application.

In the foregoing description of various modes of application of the glyphosate trimesium-photosystem II inhibitor combinations, it is inherent that each form of application requires that in some manner, the glyphosate trimesium and photosystem II inhibitor will physically combine to form a "composition" of those agents.

In field applications, the glyphosate trimesium, photosystem It inhibitor, or a mixture thereof, may be applied to the soybean plant locus without any adjuvants other than a solvent. Usually, the glyphosate trimesium, photosystem II inhibitor, or mixture thereof, is applied in conjunction with one or more adjuvants in liquid or solid form. Compositions or formulations containing mixtures of glyphosate trimesium and an appropriate photosystem II inhibitor usually are prepared by admixing the glyphosate trimesium and photosystem II inhibitor with one or more adjuvants such as diluents, solvents, extenders, carriers, conditioning agents, water, wetting agents, dispersing agents, antidrift agents, or emulsifying agents, or any suitable combination of these adjuvants. These mixtures can be in the form of particulate solids, granules, pellets, wettable powders, dusts, solutions, aqueous dispersions, or emulsions.

Application of the glyphosate trimesium, photosystem II inhibitor, or mixture thereof, can be carried out by conventional techniques utilizing, for example, hand-carried or tractor-mounted spreaders, power dusters, boom and hand sprayers, spray dusters, aircraft, and granular applicators. If desired, application of the compositions of the invention to plants can be accomplished by incorporating the compositions in the soil or other media.

The following examples are for illustrative purposes only and are not intended as necessarily representative of the overall testing performed and are not intended to limit the invention in any way. As one skilled in the art is aware, in herbicidal testing, a significant number of factors that are not readily controllable can affect the results of individual tests and render them non-reproducible. For example, the results may vary depending on environmental factors, such as amount of sunlight and water, soil type, pH of the soil, temperature, and humidity, among other factors. Also, the depth of planting, the application rate of the herbicide, the application rate of the antidote, and the ratio of the herbicide-to-antidote application, as well as the nature of crops being tested, can affect the results of the test. Results may vary from crop to crop within the crop varieties.

EXAMPLES

Example 1

The compound trimethylsulphonium chloride (a source of the TMS cation) and bentazon were applied (at the rates listed in Table 1 below) postemergence to 3"×3" pots containing pasteurized, sandy clay loam soil in which glyphosate tolerant soybeans and glyphosate tolerant corn had been sown. The soil was fortified with fertilizer (10-10-10) prior to seeding The compounds were dissolved in water and applied with a carrier volume of 200 L/ha. All treatments were replicated four times.

The pots were placed in a greenhouse and maintained under good growing conditions. The greenhouse evironmental systems provided the plants with natural and artificial lighting to attaim 12 hours of light per day. Day and night temperatures were maintained at 29° and 21° C. respectively.

Plants were grown to the V2 or 2 leaf stage prior to compound application. Plants were sprayed 30.5cm (12 inches) above the foliage with the spray solution as prepared for the pre-emergence test. The application rate was as indicated in Table 1. Treated plants were then returned to a greenhouse and watered daily without wetting the foliage. Injury to plants was evaluated 5 days after treatment ("CDAT") and 13 DAT. Injury was evaluated as percent control being the total injury to the plants due to all factors including: inhibited emergence, stunting, malformation, albinism, chlorosis, and other types of plant injury. The control ratings range from 0 to 100 percent, where 0% represents no effect with growth equal to the retreated control and where 100% represents complete kill.

The results observed are served are summarized in Table 1 below, which results are the mean of four replication

TABLE 1

| TMS (g/ha) | Bentazon (g/ha) | Soybean 5 DAT | Soybean 13 DAT | Corn 5 DAT | Corn 13 DAT |
|---|---|---|---|---|---|
| 840 | 0 | 24 | 18 | 19 | 60 |
| 420 | 0 | 15 | 13 | 14 | 48 |
| 0 | 500 | 8 | 0 | 0 | 0 |
| 0 | 250 | 2 | 4 | 0 | 0 |
| 840 | 500 | 13 | 5 | 21 | 66 |
| 840 | 250 | 16 | 5 | 15 | 66 |
| 840 | 125 | 10 | 4 | 19 | 61 |
| 840 | 63 | 9 | 4 | 15 | 69 |
| 840 | 50 | 9 | 5 | 25 | 75 |
| 840 | 32 | 6 | 6 | 19 | 70 |
| 840 | 25 | 11 | 8 | 19 | 66 |

TABLE 1-continued

| TMS (g/ha) | Bentazon (g/ha) | Soybean 5 DAT | Soybean 13 DAT | Corn 5 DAT | Corn 13 DAT |
|---|---|---|---|---|---|
| 840 | 16 | 8 | 6 | 19 | 73 |
| 840 | 8 | 16 | 18 | 19 | 73 |
| 840 | 4 | 24 | 15 | 23 | 69 |

Example 2

The same general procedure was followed as in Example 1, except that glyphosate trimesium applied instead of thylsulphonium chloride, at the rates shown in Table 2 below, and corn was not included in the trials. The results using the same rating system as Example 1 are shown in Table 2.

TABLE 2

| Glyphosate trimesium (g/ha) | Bentazon (g/ha) | Soybean 5 DAT | Soybean 13 DAT |
|---|---|---|---|
| 0 | 0 | 0 | 0 |
| 0 | 4 | 0 | 0 |
| 0 | 8 | 0 | 0 |
| 0 | 16 | 0 | 0 |
| 0 | 32 | 0 | 0 |
| 0 | 64 | 0 | 0 |
| 750 | 0 | 13 | 7 |
| 750 | 4 | 7 | 5 |
| 750 | 8 | 5 | 3 |
| 750 | 16 | 4 | 2 |
| 750 | 32 | 1 | 1 |
| 750 | 64 | 1 | 1 |
| 1500 | 0 | 37 | 27 |
| 1500 | 4 | 33 | 22 |
| 1500 | 8 | 27 | 15 |
| 1500 | 16 | 17 | 12 |
| 1500 | 32 | 13 | 8 |
| 1500 | 64 | 4 | 4 |
| 3000 | 0 | 58 | 35 |
| 3000 | 4 | 43 | 38 |
| 3000 | 8 | 40 | 32 |
| 3000 | 16 | 33 | 20 |
| 3000 | 32 | 33 | 18 |
| 3000 | 64 | 20 | 13 |

Similar safening effects were observed in additional trials at differing carrier volumes and at different application timings.

Example 3

In plots located in Champaign, Ill. (three replications), seeds of the following weed species were planted: *Digitaria sanguinalis* ("DIGSA"); *Setaria faberi* ("SETFA"); *Setaria glauca* ("SETLU");*Echinochloa crusgalli* a crusgalli ("ECHCG"); *Sorghum vulgare* ("SORVU"); *Sida spinosa* ("SIDSP"); *Ipomoea hederacea* ("IPOHE"); *Amaranthus retroflexus* ("AMARE"); *Xanthium strumarium* ("XANST"); *Helianthus annuns* ("HELAN") and *Abutilon theophrasti* ("ABUTH"). The plots were also planted with two varieties of glyphosate tolerant soybeans ("GLXMA P9294" and "GLXMA P9333"). When the soybeans had reached the 4–5 trifoliate stage, the plots were treated with glyphosate trimesium alone or glyphosate trimesium+bentazon, at the application rates indicated in Table 3. Injury to the species in each plot was tated 7 and 18 dats after application (DAA) of the glyphosate trimesium with or without bentazon and the results are shown in Table 3. The results shown in Table 3 are the mean of three replications.

TABLE 2

| | Glyphosate TMS (1.5 lb/acre) | | Glyphosate TMS (1.5 lb/acre) + bentazon (0.5 lb/acre) | | Glyphosate TMS (1.5 lb/acre) + bentazon (0.5 lb/acre)** | | Glyphosate TMS (1.5 lb/acre) + bentazon (0.25 lb/acre) | |
|---|---|---|---|---|---|---|---|---|
| | 7 DAA | 18 DAA | 7 DAA | 18 DAA | 7 DAA | 18 DAA | 7 DAA | 18 DAA |
| DIGSA | 99 | 100 | 98 | 100 | 97 | 100 | 97 | 100 |
| SETFA | 96 | 100 | 95 | 100 | 96 | 100 | 95 | 100 |
| SETLU | 95 | 100 | 67 | 100 | 82 | 100 | 72 | 100 |
| ECHCG | 67 | 94 | 37 | 90 | 47 | 90 | 50 | 90 |
| SORVU | 93 | 100 | 70 | 99 | 73 | 100 | 80 | 99 |
| SIDSP | 60 | 83 | 33 | 90 | 17 | 70 | 13 | 88 |
| IPOHE | 43 | 68 | 20 | 63 | 20 | 53 | 23 | 60 |
| AMARE | 100 | 100 | 92 | 100 | 93 | 100 | 96 | 100 |
| XANST | 99 | 100 | 96 | 100 | 96 | 100 | 95 | 100 |
| ABUTH | 40 | 80 | 50 | 83 | 40 | 68 | 50 | 78 |
| HELAN | 99 | 100 | 40 | 95 | 37 | 96 | 40 | 97 |
| GLXMA P9294 | 8 | 9 | 1 | 0 | 0 | 0 | 0 | 0 |
| GLXMA P9333 | 5 | 6 | 0 | 0 | 0 | 0 | 0 | 0 |

**All treatments except this one also included ammonium sulfate

Although the invention has been described with reference to preferred embodiments and examples thereof, the scope of the present invention is not limited only to those described embodiments. As will be apparent to persons skilled in the art, modifications and adaptations to the above-described invention can be made without departing from the spirit and scope of the invention, which is defined and circumscribed by the appended claims.

What is claimed is:

1. An herbicidal composition comprising:
   (a) an herbicidally effective amount of glyphosate trimesium; and
   (b) an antidotally effective amount of bentazon which is antidotally effective for said glyphosate trimesium.

2. An herbicidal composition according to claim 1, wherein the weight ratio of component (a) to component (b) is between about 95:1 and about 10:1.

3. An herbicidal composition according to claim 1, wherein tie weight ratio of of component (a) to component (b) is between about 47:1 and about 12:1.

4. A method of reducing expression of short term transitory cosmetic plant effect on a glyphosate tolerant soybean crop by glyphosate trimesium, which comprises applying to a locus of the glyphosate tolerant soybean crop a herbicidally effective amount of glyphosate trimesium and a non-phytotoxic antidotally effective amount of bentazon which is antidotally effective for said glyphosate trimesium.

5. A method according to claim 4 wherein the glyphosate trimesium is applied postemergently to the glyphosate tolerant soybean crop in an amount between about 280 g/ha and about 7840 g/ha and bentazon is applied in an amount of between about 5 g/ha and about 300 g/ha.

6. A method according to claim 4 wherein the glyphosate trimesium is applied postemergently to the glyphosate tolerant soybean crop in an amount of between about 750 g/ha and about 1500 g/ha and bentazon is applied in an amount of between about 32 g/ha and about 64 g/ha.

7. A method for controlling a weed in a soybean crop comprising applying to a locus of at least one of the weed and the soybean crop an herbicidally effective amount of glyphosate trimesium and an antidotally effective amount of bentazon which is antidotally effective for the glyphosate un trimesium.

8. The method of claim 7, wherein the soybean crop is a genetically modified glyphosate tolerant soybean crop.

9. The method of claim 7, wherein the glyphosate trimesium is applied in an amount between about 280 g/ha and about 7840 g/ha and the bentazon is applied in an amount between about 5 gala and about 300 g/ha.

10. The method of claim 7, wherein the glyphosate trimesium is applied in an amount between about 750 g/ha and about 1500 g/ha and the bentazon is applied in an amount between about 32 g/ha and about 64 g/ha.

11. The method of claim 7, wherein the glyphosate trimesium and bentazon are applied to the locus of at least one of the weed and the soybean crop in the form of a composition or are applied separately to the locus of at least one of the weed and the soybean crop.

12. An herbicidal composition comprising glyphosate trimesium and bentazon in a weight ratio of between about 47:1 and about 12:1.

13. A method for controlling a weed in a soybean crop comprising applying to a locus of at least one of the weed and the soybean crop glyphosate trimesium in an amount between about 750 g/ha and about 1500 g/ha and bentazon in an amount between about 32 g/ha and about 64 g/ha.

14. The method of claim 13, wherein the soybean crop is a genetically modified glyphosate tolerant soybean crop.

15. The method of claim 13, wherein the glyphosate trimesium and the bentazon are applied to the locus of at least one of the weed and the soybean crop in the form of a composition or are applied separately to the locus of at least one of the weed and the soybean.

16. An herbicidal composition comprising:
   (a) a herbicidally effective amount of glyphosate trimesium; and
   (b) an antidotally effective amount of bentazon;
      wherein the weight ratio of component (a) to cormnent (b) is between about 47:1 and about 12:1.

* * * * *